United States Patent [19]

Moorehead

[11] Patent Number: 4,562,269

[45] Date of Patent: Dec. 31, 1985

[54] METHOD OF PRODUCING MALEIC ANHYDRIDE

[75] Inventor: Eric L. Moorehead, Diamond Bar, Calif.

[73] Assignee: Union Oil Company of California, Los Angeles, Calif.

[21] Appl. No.: 492,163

[22] Filed: May 6, 1983

Related U.S. Application Data

[63] Continuation-in-part of Ser. No. 275,370, Jun. 19, 1981, abandoned, and a continuation-in-part of Ser. No. 328,446, Dec. 7, 1981, Pat. No. 4,454,245, and a continuation-in-part of Ser. No. 335,531, Dec. 29, 1981, Pat. No. 4,455,388, which is a continuation-in-part of Ser. No. 328,446, Dec. 7, 1981, Pat. No. 4,454,245.

[51] Int. Cl.$^4$ .................................... C07D 307/60
[52] U.S. Cl. .................... 549/259; 549/256; 549/257; 549/260; 502/209
[58] Field of Search ............... 549/259, 260, 256, 257

[56] References Cited

U.S. PATENT DOCUMENTS

| | | | |
|---|---|---|---|
| 1,935,054 | 11/1934 | Jaeger | 549/257 |
| 2,294,130 | 8/1943 | Porter | 549/260 |
| 3,156,705 | 11/1964 | Kerr | 549/260 |
| 3,243,385 | 3/1966 | Sennewald et al. | 252/437 |
| 3,288,721 | 11/1966 | Kerr | 502/209 |
| 3,370,081 | 2/1968 | Sennewald et al. | 260/465 |
| 3,506,400 | 4/1970 | Eberly, Jr. et al. | 23/182 |
| 3,640,681 | 2/1972 | Pickert | 252/455 |
| 3,700,749 | 10/1972 | Robinson et al. | 252/464 |
| 3,702,886 | 11/1972 | Argauer et al. | 423/328 |
| 3,751,502 | 8/1973 | Hayes et al. | 585/401 |
| 3,775,508 | 11/1973 | Pitzer | 585/654 |
| 3,789,078 | 1/1974 | Nolan et al. | 260/680 E |
| 3,856,881 | 12/1974 | Manning | 585/629 |
| 3,862,146 | 1/1975 | Boghosian | 549/260 |
| 3,867,411 | 2/1975 | Raffelson et al. | 549/260 |
| 3,884,835 | 5/1975 | Vaughn | 252/451 |
| 3,888,886 | 6/1975 | Young et al. | 549/260 |
| 3,890,218 | 6/1975 | Morrison | 208/135 |
| 3,914,332 | 10/1975 | Dickason | 585/661 |
| 3,915,892 | 10/1975 | Harrison | 252/435 |
| 3,925,447 | 12/1975 | Gelbein | 260/465 C |
| 3,927,138 | 12/1975 | Walker | 558/661 |
| 3,931,046 | 1/1976 | Weinstein et al. | 549/260 |
| 3,972,832 | 3/1976 | Butter et al. | 502/77 |
| 3,977,998 | 8/1976 | Freerks et al. | 252/435 |
| 4,061,724 | 12/1977 | Grose et al. | 423/335 |
| 4,062,873 | 12/1977 | Harrison | 252/435 |
| 4,064,070 | 12/1977 | Harrison | 252/435 |
| 4,073,865 | 2/1978 | Flanigen et al. | 423/339 |
| 4,092,269 | 5/1978 | Mount et al. | 252/435 |
| 4,104,294 | 8/1978 | Grose et al. | 252/426 |
| 4,123,388 | 10/1978 | Kerr et al. | 252/437 |
| 4,151,116 | 4/1979 | McDermott | 502/209 |
| 4,153,577 | 5/1979 | Barone | 252/437 |
| 4,165,299 | 8/1979 | Pederson | 252/435 |
| 4,165,300 | 8/1979 | Dolhyj et al. | 252/462 |
| 4,171,316 | 10/1979 | Pederson | 252/437 |
| 4,179,404 | 12/1979 | Barone | 252/435 |
| 4,206,084 | 6/1980 | Strojny et al. | 252/455 R |
| 4,244,879 | 1/1981 | Bremer et al. | 549/259 |
| 4,246,141 | 1/1981 | Hass et al. | 252/439 |
| 4,246,421 | 1/1981 | Bartek et al. | 546/352 |
| 4,247,419 | 1/1981 | Vartuli et al. | 252/435 |
| 4,252,680 | 2/1981 | Walker et al. | 252/435 |
| 4,270,017 | 5/1981 | Young | 252/437 |
| 4,283,306 | 8/1981 | Herkes | 252/432 |
| 4,292,201 | 9/1981 | Vartuli et al. | 252/435 |
| 4,292,202 | 9/1981 | Vartuli et al. | 252/435 |
| 4,309,275 | 1/1982 | Mulaskey | 208/109 |
| 4,309,276 | 1/1982 | Miller | 208/109 |
| 4,311,611 | 1/1982 | Sasaki et al. | 568/477 |
| 4,314,983 | 2/1982 | Hass et al. | 423/542 |
| 4,333,853 | 6/1982 | Milberger et al. | 252/435 |
| 4,347,395 | 8/1982 | Chu et al. | 585/420 |
| 4,360,453 | 11/1982 | Lemanski et al. | 252/435 |
| 4,361,501 | 11/1982 | Blum et al. | 252/435 |
| 4,362,653 | 12/1982 | Robinson | 252/455 R |
| 4,370,490 | 1/1983 | Gruber et al. | 560/214 |
| 4,371,457 | 2/1983 | Chu | 502/77 |
| 4,377,502 | 3/1983 | Klotz | 502/77 |
| 4,388,221 | 6/1983 | Moorehead | 252/435 |
| 4,394,300 | 7/1983 | Chu et al. | 502/77 |
| 4,396,536 | 8/1983 | Bremer et al. | 252/437 |
| 4,428,862 | 1/1984 | Ward et al. | 502/77 |
| 4,454,245 | 6/1984 | Robinson et al. | 502/209 |
| 4,454,342 | 6/1984 | Gaffney et al. | 560/204 |
| 4,455,388 | 6/1984 | Robinson | 502/209 |
| 4,481,363 | 11/1984 | Moorehead | 549/260 |

FOREIGN PATENT DOCUMENTS 35807   9/1981   European Pat. Off. .

OTHER PUBLICATIONS

Silicalite, A New Hydrophobic Crystalline Silica Molecular Sieve, by E. M. Flanigen et al., Nature vol. 271, Feb. 9, 1978.

Reactions on ZSM-5-Type Zeolite Catalysts, by J. R. Anderson et al., Journal of Catalysis 58, 114-130 (1979).

Chemical and Physical Properties of the ZSM-5 Substitutional Series, by D. H. Olson et al., Journal of Catalysis 61, 390-396 (1980).

"Advanced Inorganic," 2nd Ed., Cotton & Wilkerson, pp. 469-474 (1966).

"When is a Zeolite Not a Zeolite?" by Lovat V. C. Rees, Nature vol. 296, pp. 491-492, Apr. 8, 1982.

"Silicalite-2, A Silica Analogue of the Aluminosilicate Zeolite ZSM-11" by D. M. Bibby et al., Nature, vol. 280, pp. 664-665, Aug. 23, 1979.

(List continued on next page.)

Primary Examiner—Henry R. Jiles
Assistant Examiner—Bernard L. Dentz
Attorney, Agent, or Firm—Dean Sandford; Gregory F. Wirzbicki

[57] ABSTRACT

Large surface area oxidation catalysts suitable for converting $C_4$ to $C_{10}$ hydrocarbons to maleic anhydride are disclosed, comprising the oxides of vanadium, phosphorus and tin in combination with a crystalline silica having a surface area between 100 $M^2/g$ to 450 $M^2/g$ and wherein the vanadium has an average valence in the range of from 3.5 to 4.9.

52 Claims, No Drawings

OTHER PUBLICATIONS

"The Structure and the Activity of Vanadyl Phosphate Catalysts" by Michihiro Nakamura et al., *Journal of Catalysis*, vol. 34, pp. 345–355 (1974).

"Pentasil Family of High Silica Crystalline Materials" by G. T. Kokotailo et al., in *The Properties and Applications of Zeolites*, ed. R. P. Townsend, the Proceedings of a Conference organized jointly by the Inorganic Chemicals Group of the Chemical Society and The Society of Chemical Industry (Burlington House, London), Apr. 18–20, 1979, pp. 134–139.

"Resolving Crystallographically Distinct Tetrahedral Sites in Silicalite and ZSM-5 by Solid-State NMR" by C. A. Fyfe et al., *Nature*, vol. 296, Apr. 8, 1982, pp. 530–533.

"Research Article Triggers Dispute on Zeolite" by Budiansky, *Nature*, vol. 300, Nov. 1982, p. 309.

"Zoned Aluminium Distribution in Synthetic Zeolite ZSM-5" by Ballmoos et al., *Nature*, vol. 289, Feb. 26, 1981, pp. 782–783.

"Zeolite Molecular Sieves" by Breck, John Wiley and Sons, New York, 1974, pp. 122–124.

"McGraw-Hill Dictionary of Scientific Terms," 2nd edition, Lapedes, ed., New York, definitions of "mordenite" and "zeolite."

"Industrial Minerals and Rocks" published by American Institute of Mining, Metallurgical, and Petroleum Engineers, 1960, pp. 303–305.

Kirk–Othmer *Encyclopedia of Chemical Technology*, Third Edition, vol. 20, pp. 766–781, especially page 777.

U. S. Ser. No. 492,226, filed May 6, 1983, Eric L. Moorehead.

U.S. Ser. No. 592,422, filed Mar. 21, 1984, Eric L. Moorehead and Paul R. Robinson.

U.S. Ser. No. 595,333, filed Mar. 30, 1984, Eric L. Moorehead and Paul R. Robinson.

U.S. Ser. No. 646,291, filed Aug. 29, 1984, Eric L. Moorehead.

U.S. Ser. No. 666,997, filed Oct. 31, 1984, Eric L. Moorehead.

U.S. Ser. No. 667,000, filed Oct. 31, 1984, Paul R. Robinson and Eric L. Moorehead.

METHOD OF PRODUCING MALEIC ANHYDRIDE

RELATED APPLICATIONS

This application is a continuation-in-part of copending application Ser. No. 275,370, filed on June 19, 1981, abandoned, and also a continuation-in-part of application U.S. Ser. No. 328,446, filed Dec. 7, 1981, now U.S. Pat. No 4,454,245, and also a continuation-in-part of application U.S. Ser. No. 335,531, filed Dec. 29, 1981, now U.S. Pat. No. 4,455,388, which itself is a continuation-in-part of said application Ser. No. 328,446, filed Dec. 7, 1981, now U.S. Pat. No. 4,454,245.

BACKGROUND OF THE INVENTION

1. Field of the Invention

The present invention relates to oxidation catalysts, and more particularly to oxidation catalysts which are useful for producing maleic anhydride from $C_4$ to $C_{10}$ hydrocarbons.

2. The Prior Art

Essentially all of the catalysts and methods disclosed in the prior art for producing maleic anhydride from $C_4$ and higher hydrocarbons employ oxidation catalysts containing vanadium in a valence state of less then +5. One method of forming such catalysts is to impregnate a catalyst base with a vanadium compound in which the vanadium has a valence of less then +5. Another more desirable method involves impregnating the catalyst with a vanadium compound which has vanadium in the +5 valence state and then reducing the vanadium from the +5 valence state to a valence less than +5.

Several references disclose oxidation catalysts containing vanadium-phosphorus mixed oxide catalysts and methods of preparing the same. For example, U.S. Pat. No. 3,243,385 discloses a process for preparing a catalyst containing vanadium, tin and optionally phosphorus deposited on a carrier material. Silicic acid is described as one desirable carrier in the patent.

U.S. Pat. No. 3,867,411 relates to an oxidation process for producing maleic anhydride from $C_4$ to $C_{10}$ saturated hydrocarbons utilizing as the oxidation catalyst a composite of phosphorus, vanadium, iron, oxygen and chromium.

U.S. Pat. No. 4,061,724 describes a crystalline silica composition prepared by calcining a crystalline hydrated alkylonium silicate prepared hydrothermally from a reaction mixture containing water, amorphous silica and a quarternary ammonium compound.

U.S. Pat. No. 4,064,070 discloses a catalyst comprising vanadium, phosphorus and silicon oxides prepared by coprecipitating vanadium oxide and silica or a silica precursor. The catalyst is described as suitable for use in oxidizing a hydrocarbon feed to produce maleic anhydride.

Finally, U.S. Pat. No. 4,151,116 relates to a catalyst for oxidizing butane to produce maleic anhydride, said catalyst comprising a substrate containing phosphorus and vanadium, and optionally containing an activator and a post deposited promoter. Substrates described as suitable for use include silica gel, silica alumina, silica etc. Suitable activators include compounds of titanium, such as the halides, phosphates, sulfates and the like. The post deposited promoter is preferably a zinc salt.

As can readily be determined from the above, there is an ongoing effort to develop oxidation catalysts for preparing maleic anhydride from alkanes and olefins.

Accordingly, it is an object of the present invention to provide a large surface area oxidation catalyst for producing maleic anhydride and a method for preparing the same.

A further object of the present invention is to provide a method for obtaining improved yields and selectivity of maleic anhydride and, in addition, improvements in catalyst stability.

Another object of the present invention is to provide an improved oxidation catalyst for oxidizing saturated and unsaturated hydrocarbons to maleic anhydride.

These and other objects are accomplished according to the present invention by oxidizing either a saturated or unsaturated hydrocarbon having from four to ten carbon atoms in the presence of an oxidation catalyst comprising vanadium, phosphorus, tin and a crystalline silica.

SUMMARY OF THE INVENTION

The present invention resides in an oxidation catalyst comprising the oxides of vanadium and phosphorus in combination with crystalline silica. In addition, a tin compound, preferably tin oxide may be included as an element of the catalyst.

In another embodiment of the invention, the catalysts herein may be described by the ratio of moles of elements in the catalysts as described below:

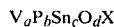

wherein X is a crystalline silica, a is from 0.10 to 1, b is 1, c is from 0.001 to 0.30, and d is a number which satisfies the valence requirements of the other elements present.

The invention additionally resides in a method of preparing a vanadium, phosphorus, tin, mixed-oxide, crystalline silica, oxidation catalyst which comprises:

(A) reacting a vanadium compound with a phosphorus compound in an acidic aqueous solution and optionally a tin compound under reaction conditions which will provide vanadium having an average oxidation state of 3.50 to 4.90 to form a catalyst precursor, (B) reacting the catalyst precursor with a binder, solvent and crystalline silica to form an impregnated crystalline silica, and (C) calcining the oxidation catalyst at temperatures in the range of from 400° F. to 1,200° F., for from ½ hour to 6 hours.

A method for producing maleic anhydride is disclosed which comprises reacting a $C_4$ to $C_{10}$ hydrocarbon feedstock with a gas containing molecular oxygen in the vapor phase, under reaction conditions in the presence of an oxidation catalyst comprising the oxides of vanadium and phosphorus and a crystalline silica. Optionally, tin, preferably as the oxide, may be an element of the catalyst.

DETAILED DESCRIPTION OF THE INVENTION

Broadly described, the catalyst of this invention comprise compounds of vanadium and phosphorus composited on a crystalline silica, with preferred crystalline silicas being molecular sieves having a substantial portion of pores having a diameter of 6Å or less, preferably between about 5Å and 6Å. The catalysts herein may optionally include a tin compound as an element thereof. Preferably, the vanadium, phosphorus and tin compounds are present in the catalyst as the oxide.

Generally, the catalysts of this invention have the following ratio of moles:

$$V_aP_bSn_cO_dX$$

wherein X is a crystalline silica, a is from 0.10 to 1, b is 1, and c is from 0 to 0.30, preferably 0.001 to 0.30. The above molar ratios are not an empirical formula, however, the numbers assigned to the subscript letters, i.e., a, b, and c represent the atomic ratio of the respective V, P and Sn active components of the catalyst. The d, in the above formula, may vary widely depending on the mixed oxide combination within the catalyst complex. The only restriction of the d value is that the number assigned to d must satisfy the valency requirements of vanadium, phosphorus and tin in the catalyst complex.

Generally, oxygen combines with the vanadium, phosphorus and tin to form a catalyst precursor which is an oxygen complex or the oxides of these compounds. The oxygen content of the catalyst precursor will vary depending upon the oxidation state of the vanadium, phosphorus and tin utilized. However, d will normally have a value of from 2 to 12, especially from 2 to 8.

The vanadium compounds useful as a source of vanadium in the catalyst precursor are those vanadium compounds known to the art. Suitable vanadium compounds include vanadium salts, such as ammonium metavanadate and vanadyl sulfate; vanadium oxides, such as vanadium pentoxide; and vanadium oxyhalides, such as vanadium oxytrichloride. However, pentavalent vanadium compounds such as ammonium metavanadate and vanadium pentoxide are preferred.

The phosphorus compounds useful as a source of phosphorus in the catalyst precursor are also those known to the art. Suitable phosphorus compounds are selected from phosphoric acid, phosphorus pentoxide, ammonium phosphate and diammonium phosphate. The preferred phosphorus compounds are pentavalent phosphorus compounds such as phosphoric acid and phosphorus pentoxide.

Suitable tin compounds are those tin compounds which have a valence of +2, since the tin compound acts as a reducing agent for the vanadium compound in the catalyst. Tin compounds useful herein preferably are selected from stannous chloride, stannous fluoride, stannous bromide, stannous oxide, stannous sulfate, stannous acetate and stannous oxalate. Upon reaction of the tin compound with the vanadium compound, tin +2 (stannous) will be oxidized up to the tin +4 (stannic) oxidation state and vanadium in the +5 oxidation state will be reduced to an average oxidation state of less than +5.

The catalyst precursor is preferably produced by dissolving and mixing compounds of vanadium, phosphorus and optionally tin in an acidic-aqueous medium such as water and hydrochloric acid, hydroiodic acid, hydroformic acid, acetic acid, oxalic acid, maleic acid, citric acid or formic acid. The vanadium-phosphorus-tin compounds are contacted at an atomic ratio of vanadium-phosphorus-tin of from 0.10:1:0.001 to 1:1:0.30, especially from 0.20:1:0.002 to 1:1:0.20. The atom ratio of vanadium to phosphorus in the starting material is important since it controls the vandium to phosphorus atom ratio in the final catalyst. When the oxidation catalysts herein contain a vanadium-phosphorus atom ratio below 0.10:1.00 or above 1.00, the yield of maleic anhydride using these catalysts is so low as to render the reaction commercially unattractive. It should be noted that phosphorus aids in stabilizing vanadium in the final catalyst composition, while tin +2 acts as a reducing agent which aids in the reduction of vanadium to a valency state of less than +5. It should additionally be noted that the above-described acids which dissolve the vanadium, phosphorus and tin compounds act as reducing agents for the vanadium compounds. However, the reduction process takes from one-half hour to about one hour when tin is not present in the reaction medium. Upon the addition of tin to the reaction medium, the reduction of vanadium to a valency of less than +5 takes place almost instantly, i.e., less than one minute. Generally, the vanadium is reduced to an average valence within the range of from +3.50 to +4.90, preferably from +4.10 to 4.70.

Conventional apparatus and techniques known to the art may be used to dissolve and react the components which make up the catalyst precursor. For example, temperatures of from 100° F. to 220° F., especially from 180° F. to 220° F. and a reaction time of from ½ hour to 20 hours under atmospheric pressure normally are sufficient to dissolve and react the vanadium, phosphorus and tin compounds. However, pressures from atmospheric pressure to 50 p.s.i.g. may be used to shorten the dissolution and reaction times. Generally, agitation is supplied during the reaction period to ensure complete contact of the reactants. Agitation is defined herein as mixing, rocking, shaking, etc.

After the reaction proceeds to completion the catalyst precursor is concentrated and collected using conventional methods and techniques and mixed with a crystalline silica to form an impregnated crystalline silica.

The preferred crystalline silica composition herein is characterized by pores of uniform diameter of 6Å or less, and even more preferably 5Å to 6Å and is prepared by calcining a crystalline hydrated alkylonium silica prepared by hydrothermal crystallization from a reaction mixture containing as essential reagents, water, amorphous silica and a quarternary ammonium compound, for example, tetraethyl ammonium hydroxide, at a pH of at least 10. The compound thus formed is calcined to decompose the alkylonium moieties present. The crystalline silica exhibits no ion exchange properties; however, because of its uniform pore structure it is capable of making size-selective separations of molecular species.

The crystalline silica produced from the above-described mixture, has a topological type of tetrahedral framework, which contains a large fraction of five-membered rings of silica-oxygen tetrahedra. The framework comprises a three-dimensional system of intersecting channels which are defined as ten rings of oxygen atoms extending in three directions. Precursor-organic nitrogen ions which occupy the intersecting channels, are removed by heating or in the alternative, by extracting with an acid to yield the desired crystalline silica. The resulting void volume occupies approximately 33 percent of the crystal structure, and the three-dimensional channel is wide enough to absorb organic molecules having up to about 6Å in diameter. The crystalline silica, herein, degrades to glass products and dense crystalline silica above about 2,732° F.

The crystalline silica in this invention is analogous to highly siliceous alkali silicates which form as insoluble compounds during extended hydrothermal digestion. The organic agent in the form of a nitrogen compound incorporated as a cation during crystallization of the crystalline silica herein, becomes a source of micropores when eliminated by combustion or extraction. The surface of these micropores are relatively free of hydroxyl groups. The isolated hydroxyl groups which are present provide a moderate acidic strength when the crystalline silica is thermally activated. The crystalline silica is a uniquely, active solid which is suitable for use as a catalyst component or in catalysts used in hydrocarbon reactions.

The crystalline silica provides not only the required surface for the catalyst precursor, but gives physical strength and stability to the catalyst material. In addition, the crystalline silica has a large surface area upon which the catalyst precursor is deposited.

A particularly preferred crystalline silica suitable for use herein which exhibits molecular sieve properties is termed silicalite. This compound has a specific gravity at 25° C. of 1.99±0.05 g/cc as measured by water displacement. After calcination at 600° C. in air for 1 hour, silicalite has a specific gravity of 1.70±0.05 g/cc. The mean refractive index of silicalite crystals measured as the as synthesized form is 1.48±0.01, while the calcined form (600° C. in air for 1 hour) is 1.39±0.01.

The x-ray diffraction pattern of silicalite after calcination in air at 600° C. for 1 hour has as its six strongest lines or interplanar spacings $d=11.1\pm0.2$, $d=10.0\pm0.2$, $d=3.85\pm0.07$, $d=3.82\pm0.07$, $d=3.76\pm0.05$ and $d=3.72\pm0.05$.

The pore diameter of silicalite is about 6 A and its pore volume is 0.18 cc/g as determined by adsorption. The uniform pore structure of silicalite imparts size-selective molecular sieve properties to the composition. These molecular sieve properties permit the separation of P-xylene from O-xylene, m-xylene and ethylbenzene. A more detailed description of silicalite including a method of how to prepare the composition is described in greater detail in U.S. Pat. No. 4,061,724, the disclosure of which is incorporated herein by reference.

The crystalline silicas herein exhibit molecular sieve properties characteristic of certain crystalline aluminosilicate compositions, but exhibit substantially none of the ion-exchange properties which are essential to the aluminosilicates commonly referred to as zeolites. The lack of ion-exchange properties in the crystalline silicas herein is due to the crystal lattice structure of the silicas which does not contain alumina as an integral part of said crystal lattice.

Aluminosilicate catalysts with an aluminum content of approximately 20 weight percent or greater are not suitable for use as oxidation catalysts herein because the aluminum reacts with the phosphorus, effectively binding the phosphorus to aluminum and altering the oxidation characteristics of the catalyst. Thus, these type carriers are not desirable for use as substrates in the oxidation catalysts herein Generally, from 15 to 50 weight percent of the catalyst precursor comprising the oxides of vanadium, phosphorus and optionally tin, is mixed with from 85 to 50 weight percent of the crystalline silica. Binding agents and additives may optionally be added to the catalyst to provide the proper consistency of the catalyst prior to mixing and forming said catalyst. The binding agents and additives, when used, preferably comprise from 0 to 10, especially from 3 to 10 weight percent of the finished catalyst. Suitable binding agents include methocel (methyl cellulose), Siloid 65 (an amorphous silica), and alumina. Additives suitable for use herein include organic polar solvents such as ethanol, propanol, isopropanol, butanol, benzene, etc. The binding agents and additives are normally mixed in a weight ratio of from 1:20 to 10:1. The preferred method of mixing the catalyst precursor and crystalline silicate is by co-mulling. However, other conventional mixing techniques may be used.

It should be noted that the color of the calcined catalysts herein is indicative of the average oxidation state of the vanadium deposited in the catalyst. A color of dark grey indicates an average oxidation state of below 3.5 for the vanadium, while an orange or yellow color for the catalyst is indicative of an average oxidation state for vanadium of greater than 5. These two average oxidation states for vanadium will not oxidize alkanes and olefins to maleic anhydride. The preferred crystalline silica catalysts herein have a catalyst color of light to dark green after calcination. This green color indicates an average oxidation state of 3.5 to 4.9 for the vanadium in the catalyst. These catalysts have the requisite average oxidation state for vanadium and are suitable for oxidizing $C_4$ to $C_{10}$ alkanes and olefins to maleic anhydride.

The physical form of the catalysts of this invention depends to a large extent upon the technique of drying and/or the desired shape. The catalysts may be produced as spheres, pellets, beads, elongated cylinders, and three-lobe or cloverleaf configurations. For example, the composites may be filtered and oven dried and course granules may be obtained by breaking up and sieving the oven-dried cake up to any desired size. Spray drying the catalyst, such that, the dried catalyst will pass through a 4 to 200 mesh sieve (U.S.) is another method of producing the desired catalyst. Another method involves shapeboring the catalyst into a desired configuration using a restraint to maintain the desired shape and drying the catalyst. A particularly desirable shape is a cylindrical configuration having a diameter of from 1/16 inch to ⅛ inch and a length of from ¼ inch to ½ inch.

The final catalyst is activated by calcination which preferably is performed in an air or oxygen atmosphere at a temperature of from about 400° F. to about 1,200° F., for about ¼ hour to about 6 hours, especially from about ½ hour to about 4 hours.

The catalyst thus produced is especially suited for oxidizing $C_4$ to $C_{10}$ hydrocarbons to maleic anhydride, and preferably has a surface area of from 100 $M^2/g$ to 450 $M^2/g$, a pore volume of from 0.1 cc/g to 0.8 cc/g and a compacted bulk density of from 0.5 to 1.5 g/cc.

The above described catalysts of the present invention are useful for producing maleic anhydride from $C_4$ to $C_{10}$ hydrocarbons. A variety of reactors may be used in the oxidation reactions herein. For example, conventional fluidized bed reactors and fixed-bed or tube, heat exchanger type reactors are satisfactory, the details of the operation of such reactors are well known to those skilled in the art. The oxidation reaction is an exothermic reaction, thus, necessitating relatively close control of the reaction temperature. It is desirable to have the surface of the reactor at a constant temperature and some medium may be necessary to conduct heat away from the reactor to aid temperature control. Examples of desirable mediums include molten sulfur, mercury, molten lead, or eutectic salt baths, for example a sodium nitrate-sodium nitrite-potassium nitrate eutectic constant temperature mixture. An additional method of temperature control is to use a metal block reactor whereby the metal surrounding the reactor chamber acts as a temperature regulating body or by conventional heat exchangers.

Normally a reaction mixture of a gaseous feed stream comprising a molecular oxygen containing gas, for example, air, a mixture of air and oxygen, mixtures of carbon dioxide and oxygen or mixtures of nitrogen or steam with air or oxygen, and a $C_4$ to $C_{10}$ hydrocarbon is charged to a reaction zone, for example, a conventional pressure reactor. The gaseous feed stream generally will contain a molecular oxygen containing gas and from about 0.1 to about 2.5 mole percent, especially from about 0.1 to about 1.5 mole percent of a $C_4$ to $C_{10}$ hydrocarbon for optimum yield of maleic anhydride. Although higher concentrations of hydrocarbon may be employed, they are not recommended because explosive hazards may be encountered.

The $C_4$ to $C_{10}$ hydrocarbons which are suitable for use are selected from straight and branched chain, and cyclic alkanes or olefins. Suitable $C_4$ to $C_{10}$ alkanes include butane, pentane, isopentane, cyclopentane, hexane, cyclohexane, heptane cycloheptane, octane, nonane or decane or mixtures thereof. Olefins which may be used to produce maleic anhydride are selected from mono and di olefins containing 4 to 10 carbon atoms. For example, desirable olefins include butene, butadiene, pentene, cyclopentene, hexene, cyclohexene, heptene, cycloheptene, octene, nonene or decene or mixtures thereof.

Preferably the gaseous feed stream comprising a gas containing molecular oxygen and a $C_4$ to $C_{10}$ hydrocarbon are reacted in the presence of a crystalline silica, oxidation catalyst as described herein. The crystalline silica catalyst, preferably contains oxides of vanadium, phosphorus and optionally tin in addition to the crystalline silica. The flow rate of the gaseous feed stream through the pressure reactor may be varied within rather wide limits but a preferred flow rate consists of a gas hourly space velocity (GHSV) of from 700 to 5,000 reciprocal hours.

The temperature of reaction may be varied within some limits, but normally the reaction should be conducted at temperatures within a rather critical range. The overall temperature range for the $C_{b4}$ to $C_{10}$ hydrocarbons preferably is from 500° F. to 1,200° F., especially from 600° F. to 1,000° F. It should be noted that the optimum oxidation temperatures for the alkanes and olefins differ. For example, the optimum oxidation temperature range for the $C_4$ to $C_{10}$ alkanes is from 750° F. to 1,200° F., preferably from 800° F. to 1,000° F. While the optimum oxidation temperature range for the olefins herein is from 500° F. to 900° F., especially from 600° F. to 900° F.

Typically, the reaction pressure is from atmospheric pressure to 200 p.s.i.g., preferably from atmospheric pressure to 50 p.s.i.g., as previously stated, the reaction may be carried out in any reactor suitable for effecting vapor-phase oxidation reactions, but preferably a fixed catalyst bed is employed.

The invention is further illustrated by the following examples which are illustrative of various aspects of the invention and are not intended as limiting the scope of the invention as defined by the appended claims.

EXAMPLE I

An oxidation catalyst is prepared by charging 14.13 grams of ammonium metavanadate and 100 ml of water to a 500 cc round bottom flask equipped with a water cooled condensor, heating mantle and magnetic stirrer. The above solution is heated to a temperature of 130° F. and agitated with the magnetic stirrer for 3 minutes. Next, 61.13 grams of 85 percent phosphoric acid is added to the round bottom flask with continued heating and stirring for an additional 5 minutes. The solution turns a red-orange color. Then, 20 ml of 95 percent ethanol and 20 ml of concentrated hydrochloric acid are added to the solution. The non-homogeneous solution exhibits a brown color which is slowly replaced by a green color. After an additional 5 minutes of heating and mixing, 0.91 gram of stannous chloride is added to the solution. Finally, the solution is refluxed for 16 hours.

The dark green slurry produced above (150 ml) and 200 grams of silicalite are co-mulled with 20 grams of siloid 65 (an amorphous silica) and 2 grams of methocel (methyl cellulose) to achieve the proper consistency, using a model no. 472 Lancaster Mixer, manufactured commercially by the Posey Iron Works, Inc., Lancaster, Pennsylvania. The Mixer is operated at a speed of 36 RPM. The resulting catalyst is extruded into cylindrical extrudates having an average length of ½ inch and an average diameter of 1/16 inch. The catalyst is activated by calcination at 932° F. in air for 3 hours and has a vanadium-phosphorus-tin atomic ratio of 0.23:1:0.009. The catalyst has a surface area of 207 $M^2/g$ and the vanadium has an average oxidation state of 4.10.

EXAMPLE II

An oxidation catalyst having an average oxidation state of 4.65 for the vanadium and a surface area of 298 $M^2/g$ is prepared by charging 28 grams of ammonium metavanadate and 100 ml of water to a 500 cc round bottom flask equipped with a water cooled condensor, heating mantel and magnetic stirrer. The above mixture is heated to a temperature of 130° F. with agitation for 3 minutes. Next, 60 grams of 85 percent phosphoric acid is added to the round bottom flask with continued heating and agitation for an additional 5 minutes. A mixture comprising 3.6 grams of stannous chloride dissolved in 20 ml of ethanol and 20 ml of hydrochloric acid is added to the round bottom flask and the resulting mixture is refluxed for 26 hours.

Silicalite and 150 ml of the above-described resulting mixture are co-mulled with 20 grams of siloid 65 and 4 grams of methocel using a model No.1 472. Lancaster Mixer as described in Example I. The resulting catalyst is extruded into cylindrical extrudates having an average length of ½ inch and an average diameter of 1/16 inch. The catalyst is activated by calcination at 932° F. in air for 3 hours. The final catalyst contains vanadium-phosphorus-tin in an atomic ratio of 0.42:1:0.025.

EXAMPLE III

The procedure of Example II is followed to produce an oxidation catalyst with the following exceptions:

2.8 grams of ammonium vanadate, 10 ml of water, 3 grams of phosphoric acid, 0.36 gram of stannous chloride, 2.0 ml of ethanol, 2.0 ml of hydrochloric acid, 20 grams of silicalite, 0.20 grams of methocel, and 2.0 grams of siloid 65 are used to prepare the catalyst composition. The resulting catalyst has a surface area of 325

$M^2/g$, an average oxidation state of 4.89 for the vanadium and a vanadium-phosphorus-tin atomic ratio of 0.68:1:0.054.

EXAMPLE IV

A catalyst suitable for oxidizing $C_4$ and $C_{10}$ hydrocarbons to maleic anhydride is prepared by charging 2.8 grams oF ammonium vanadate and 10 ml of water to a 100 cc flask equipped with a water cooled condenser, heating mantel and magnetic stirrer. The above mixture is heated to a temperature of 130° F. with agitation for 3 minutes. Next, 6 grams of 85% phosphoric acid is added to the round bottom flask with continued heating and agitation for an additional 5 minutes. A mixture comprising 0.36 gram of stannous chloride dissolved in 2 ml of ethanol and 2 ml of hydrochloric acid is added to the round bottom flask and the resulting mixture is refluxed for 16 hours.

Silicalite (20 grams) and 15 ml of the above-described resulting mixture are mixed with 2 grams of siloid 65 and 0.20 grams of methocel using a model no. 472 Lancaster Mixer as described in Example I. The resulting catalyst is dried at 230° F. for 2 hours and crushed to an average size of 20 to 30 mesh. The catalyst is activated by calcination at 932° F. in air for 3 hours. The final catalyst has a surface area of 299 $M^2/g$, a vanadium-phosphorus-tin atomic ratio of 0.43:1:0.035, and contains vanadium having an average oxidation state of 4.71.

EXAMPLE V

An oxidation catalyst having a surface area of 262 $M^2/g$, and containing vanadium having an average oxidation state of 4.16, is prepared according to the procedure described in Example IV with the following exception:

9 grams of 85% phosphoric acid is used in the reaction. The final catalyst has a vanadium-phosphorus-tin atomic ratio of 0.30:1:0.023.

EXAMPLE VI

An oxidation catalyst suitable for oxidizing $C_4$ to $C_{10}$ hydrocarbons to maleic anhydride is prepared according to the procedure described in Example IV with the following exception:

15 grams of 85% phosphoric acid is used. The atomic ratio of vanadium-phosphorus-tin in the catalyst is 0.16:1:0.010 and the vanadium has an average oxidation state of 3.64. The final catalyst after calcination has a surface area of 162 $M^2/g$.

EXAMPLE VII

An oxidation catalyst is prepared by charging 14.13 grams of ammonium metavanodate and 100 ml of water to a 500 cc round bottom flask equipped with a water cooled condenser, heating mantle and magnetic stirrer. The above solution is heated to a temperature of 130° F. and agitated with the magnetic stirrer for 3 minutes. Next, 61.13 grams of 85 percent phosphoric acid is added to the round bottom flask with continued heating and stirring for an additional 5 minutes. The solution turns a red-orange color. Then, 20 ml of 95 percent ethanol and 20 ml of concentrated hydrochloric acid are added to the solution. The solution exhibits a brown color which is slowly replaced by a green color. Finally, the solution is refluxed for 16 hours.

The dark green slurry produced above (150 ml) nd 200 grams of silicalite are co-mulled with 20 grams of siloid 65 (an amorphous silica) and 2 grams of methocel (methyl cellulose) to achieve the proper consistency, using a model no. 472 Lancaster Mixer, manufactured commercially by the Posey Iron Works, Inc., Lancaster, Pa. The mixer is operated at a speed of 36 RPM. The resulting catalyst is extruded into cylindrical extrudates having an average length of ½ inch and an average diameter of 1/16 inch. The catalyst is activated by calcination at 932° F. in air for 3 hours and has a vanadium-phosphorus atomic ratio of 0.23:1.00.

EXAMPLE VIII

A catalyst is prepared by charging 5.6 grams of ammonium metavanodate and 20 ml of water to a 100 cc round bottom flask equipped with a water cooled condensor, heating mantle and magnetic stirrer. The above solution is heated to a temperature of 130° F. and agitated with the magnetic stirrer for 3 minutes. Next, 15 grams of 85 percent phosphoric acid is added to the round bottom flask with continued heating and stirring for an additional 5 minutes. Then, 4 ml of 95 percent ethanol and 4 ml of concentrated hydrochloric acid are added to the solution. After an additional 5 minutes of heating and mixing, 0.72 gram of stannous chloride is added to the solution. Finally, the solution is refluxed for 16 hours.

The slurry produced above and 48 grams of a Linde type Y molecular sieve(1) are co-mulled with 4 grams siloid 65 (an amorphous silica) using a model no. 472 Lancaster mixer (see Example I). The Mixer is operated at a speed of 36 RPM. The slurry and type Y molecular sieve above have a yellowish color when mixed indicating that the average oxidation state of vanadium is too high. The resulting catalyst is extruded into cylindrical extrudates having an average diameter of 1/16 inch and activated by calcination at 932° F. in air for 3 hours. (1) Linde type Y molecular sieve—a Y type zeolite molecular sieve having a $SiO_2$ content of 72.2 weight percent and an $al_2O_3$ content of 22.8 weight percent, marketed commercially by the Union Carbide Company under the tradename Catalyst Base LZ-Y82.

EXAMPLE IX

Maleic anhydride is produced from n-butane by charging 25 ml of the catalyst of Example II to a reactor containing 82 ml of 4 to 6 mesh quartz granules. An additional 45 ml of 4 to 6 mesh quartz granules are added to the top of the catalyst as a preheat zone and n-butane distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. Air is charged to the reactor at the rate of 2.1 Stan.dard Cubic Feet (SCF)/hour and n-butane is charged to the reactor at a rate of 0.021 SCF/hour. The Gas Hourly Space Velocity (GHSV) is 2,400 hours$^{-1}$ and the catalyst bed temperature is 952° F. at atmospheric pressure. After 550 hours on stream, analysis indicates that 19.3 percent of the n-butane is converted to maleic anhydride, with a selectivity of 100 weight percent and a yield of 20.49 weight percent to maleic anhydride production.

EXAMPLE X

The procedure of Example IX is used to produce maleic anhydride with the following exceptions:

Pentane is substituted for the butane, the reaction temperature is 919° F. and the feed stream comprises air containing 1.47 mole percent pentane. After 300 hours on stream, analysis indicates that 19.6 percent of the pentane is converted to maleic anhydride with a selectivity of 100 weight percent and a yield of 22.31 weight percent to maleic anhydride production.

EXAMPLE XI

Maleic anhydride is produced from hexane by charging 25 ml of the catalyst of Example II to a reactor containing 82 ml of 4 to 6 mesh quartz granules. An additional 45 ml of 4 to 60 mesh quartz granules are added to the top of the catalyst preheat zone and hexane distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. Air is charged to the reactor at the rate of 2.1 Standard Cubic Feet (SCF)/hour and hexane is charged to the reactor at a rate of 0.021 SCF/hour. The gas hourly space velocity (GHSV) is 2,400 hours$^{-1}$ and the catalyst bed temperature is 952° F. at atmospheric pressure. After 450 hours on stream, analysis indicates that 45.9 percent of the hexane is converted to maleic anhydride, with a selectivity of 100 weight percent and a yield of 36.67 weight percent to maleic anhydride production.

EXAMPLES XII TO XVII

Maleic anhydride is produced from butene by charging 25 ml of the catalyst of Example I to a reactor containing 82 ml of 4 to 6 mesh quartz granules. An additional 45 ml of 4 to 6 mesh quartz granules are added to the top of the catalyst as a preheat zone and butene distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. A feed stream comprising air containing 1.0 mole percent of butene is charged to the reactor at the rate of 2.1 Standard Cubic Feet (SCF)/hour. The reaction is conducted at atmospheric pressure. In addition, the temperature and gas hourly space velocity (GHSV) are varied in accordance with Table I below.

TABLE 1

| Ex | GHSV (Hours$^{-1}$) | T (°F.) | Weight Percent Conversion | Selectivity | Yield |
|---|---|---|---|---|---|
| XI | 1,400 | 873 | 100 | 42 | 42 |
| XII | 1,400 | 841 | 100 | 54 | 54 |
| XIII | 1,400 | 804 | 100 | 56 | 56 |
| XIV | 900 | 767 | 98 | 75 | 74 |
| XV | 900 | 707 | 94 | 69 | 62 |
| XVI | 1,200 | 707 | 84 | 52 | 44 |

Obviously, many modifications and variations of this invention, as hereinbefore set forth, may be made without departing from the spirit and scope thereof, and therefore only such limitations should be imposed as are indicated in the appended claims.

I claim:

1. A method for producing maleic anhydride which comprises reacting a feedstream comprising a gas containing molecular oxygen and a $C_4$ to $C_{10}$ hydrocarbon under reaction conditions, in contact with a catalyst comprising vanadium and phosphorus in combination with a microporous crystalline silica.

2. The method defined in claim 1, wherein the catalyst contains tin.

3. The method defined in claim 2, wherein the hydrocarbon is a $C_4$ to $C_{10}$ alkane.

4. The method defined in claim 3, wherein the $C_4$ to $C_{10}$ alkane is a member selected from the group consisting of butane, pentane, isopentane, cyclohexane, hexane, heptane, cycloheptane, octane, nonane and decane and mixtures thereof.

5. The method defined in claim 1, wherein the hydrocarbon is a $C_4$ to $C_{10}$ olefin.

6. The method defined in claim 5, wherein the $C_4$ to $C_{10}$ olefin is a member selected from the group consisting of butene, 1, 3, butadiene, pentene, cyclopentene, hexene, cyclohexene, heptene, cycloheptene, octene, nonene and decene and mixtures thereof.

7. The method defined in claim 1, wherein the gas is a member selected from the group consisting of air and mclecular oxygen and mixtures thereof.

8. The method defined in claim 1, wherein the feedstream comprises a gas containing molecular oxygen and from 0.1 to about 2.5 mole percent of a $C_4$ to $C_{10}$ hydrocarbon.

9. The method defined in claim 6, wherein the reaction conditions comprise a temperature from 500° F. to 1,200° F., a pressure of from atmospheric pressure to 200 p.s.i.g., and a gas hourly space velocity of from 700 to 5,000 reciprocal hours.

10. A method for producing maleic anhydride which comprises reacting a feedstream comprising a gas containing molecular oxygen and a $C_4$ to $C_{10}$ alkane in the vapor phase, under reaction conditions in contact with a catalyst having the following mole ratio:

$$V_a P_b Sn_c O_d X$$

wherein X is a microporous crystalline silica, a is 0.01 to 1, b is 1, c is 0.001 to 0.30 and d is a number which satisfies the valence requirements of the vanadium, phosphorus and tin present.

11. The method defined in claim 10 wherein the $C_4$ to $C_{10}$ alkane is a member selected from the group consisting of butane, pentane, hexane, heptane, octane, nonane and decane and mixtures thereof.

12. The method defined in claim 10, wherein the gas is a member selected from the group consisting of air and oxygen and mixtures thereof.

13. The method defined in claim 10, wherein the feedstream comprises a gas containing molecular oxygen and from 0.1 to 2.5 mole percent of a $C_4$ to $C_{10}$ alkane.

14. The method defined in claim 10 wherein the reaction conditions comprise a temperature from 750° F. to 1,200° F., a pressure of from atmospheric pressure to 200 p.s.i.g., and a gas hourly space velocity of from 700 to 5,000 reciprocal hours.

15. A method for producing maleic anhydride which comprises reacting a feedstream comprising a gas containing molecular oxygen and a $C_4$ to $C_{10}$ olefin in the vapor phase, under reaction conditions in contact with a catalyst having the following mole ratio:

$$V_a P_b Sn_c O_d X$$

wherein X is a microporous crystalline silica, a is 0.10 to 1, b is 1, c is 0.001 to 0.30 and d is a number which satisfies the valence requirements of the vanadium, phosphorus and tin present.

16. The method defined in claim 15, wherein the C$_4$ to C$_{10}$ olefin is a member selected from the group consisting of butene, 1, 3 butadiene, pentene, hexene, heptene, octene, nonene and decene and mixtures thereof.

17. The method defined in claim 15, wherein the gas is a member selected from the group consisting of air and oxygen and mixtures thereof.

18. The method defined in claim 15, wherein the feedstream comprises a gas containing molecular oxygen and from 0.1 to 2.5 mole percent of a C$_4$ to C$_{10}$ olefin.

19. The method defined in claim 15, wherein the reaction conditions comprise a temperature of from 500° F. to 900° F., a pressure of from atmospheric pressure to 200 p.s.i.g., and a gas hourly space velocity of from 700 to 5,000 reciprocal hours.

20. A method for producing maleic anhydride which comprises reacting a feedstream comprising a gas containing molecular oxygen and a C$_4$ to C$_{10}$ hydrocarbon in the vapor phase at a temperature of from 300° F. to 1,200° F., a pressure of from atmospheric pressure to 200 p.s.i.g., and a gas hourly space velocity of from 700 to 5,000 reciprocal hours, in contact with a catalyst comprising vanadium, phosphorus and tin in combination with silicalite.

21. The method defined in claim 20, wherein the hydrocarbon is a C$_4$ to C$_{10}$ alkane.

22. The method defined in claim 21, wherein the C$_4$ to C$_{10}$ alkane is a member selected from the group consisting of butane, pentane, hexane, heptane, octane, nonane and decane and mixtures thereof.

23. The method defined in claim 20, wherein the hydrocarbon is a C$_4$ to C$_{10}$ olefin.

24. The method defined in claim 23, wherein the C$_4$ to C$_{10}$ olefin is a member selected from the group consisting of butene, 1, 3 butadiene, pentene, hexene, heptene, octene, nonene or decene or a mixture thereof.

25. The method defined in claim 20, wherein the gas is a member selected from the group consisting of air and oxygen and mixtures thereof.

26. The method defined in claim 20 wherein the feedstream comprises a gas containing molecular oxygen and from 0.1 to 2.5 mole percent of a C$_4$ to C$_{10}$ hydrocarbon.

27. A method for producing maleic anhydride, which comprises reacting a feedstream comprising a gas containing molecular oxygen and a C$_4$ to C$_{10}$ alkane in the vapor phase at a temperature of from 750° F. to 1,200° F., a pressure of from atmospheric pressure to 200 p.s.i.g., and a gas hourly space velocity of from 700 to 5,000 reciprocal hours, in contact with a catalyst comprising vanadium, phosphorus and a crystalline silica molecular sieve.

28. The method defined in claim 27 wherein the catalyst contains tin.

29. The method defined in claim 27 wherein the C$_4$ to C$_{10}$ alkane is a member selected from the group consisting of butane, pentane, hexane, heptane, octane, nonane and decane and mixtures thereof.

30. The method defined in claim 22 wherein the gas is a member selected from the group consisting of air and oxygen and mixtures thereof.

31. The method defined in claim 27 wherein the feedstream comprises a gas containing molecular oxygen and from 1.0 to 2.5 mole percent of a C$_4$ to C$_{10}$ alkane.

32. A method for producing maleic anhydride which comprises reacting a feedstream comprising a gas containing molecular oxygen and a C$_4$ to C$_{10}$ olefin in the vapor phase, at a temperature of from 300° F. to 900° F., a pressure of from atmospheric pressure to 200 p.s.i.g., and a gas hourly space velocity of from 700 to 5,000 reciprocal hours in contact with a catalyst comprising vanadium, phosphorus and a crystalline silica molecular sieve.

33. The method defined in claim 32, wherein the catalyst contains tin.

34. The method defined in claim 32, wherein the C$_4$ to C$_{10}$ olefin is a member selected from the group consisting of butene, 1, 3 butadiene, pentene, hexene, heptene, octene, nonene and decene and mixtures thereof.

35. The method defined in claim 32, wherein the gas is a member selected from the group consisting of air and oxygen and mixtures thereof.

36. The method defined in claim 32, wherein the feedstream comprises a gas containing molecular oxygen and from 0.1 to 2.5 mole percent of a C$_4$ to C$_{10}$ olefin.

37. A method for producing maleic anhydride, which comprises reacting a feedstream comprising air containing from 0.1 to 2.5 mole percent of butane in the vapor phase at a temperature of from 750° F. to 1,200° F., a pressure of from atmospheric pressure to 200 p.s.i.g. and a gas hourly space velocity of from 700 to 5,000 reciprocal hours, in contact with a catalyst comprising vanadium, phosphorus, tin and silicalite.

38. A method for producing maleic anhydride, which comprises reacting a feedstream comprising air containing from 0.1 to 2.5 mole percent of butene in the vapor phase at a temperature of from 300° F. to 900° F., a pressure of from atmospheric pressure to 200 p.s.i.g. and a gas hourly space velocity of from 700 to 5,000 reciprocal hours, in contact with a catalyst comprising vanadium, phosphorus, tin and silicalite.

39. A process for oxidizing a hydrocarbon in the presence of an oxidation catalyst which comprises contacting a hydrocarbon in the gas phase with a catalyst comprising vanadium, phosphorus, and a microporous crystalline silica under oxidizing conditions producing maleic anhydride.

40. The process defined in claim 39 wherein the catalyst includes tin.

41. The process defined in claim 39 including contacting the hydrocarbon with the catalyst in the presence of a gas containing molecular oxygen.

42. A process for oxidizing a hydro-carbon with an oxidation catalyst which comprises contacting a C$_4$ to C$_{10}$ hydrocarbon with a catalyst comprising vanadium, phosphorus, tin and a microporous crystalline silica under oxidizing conditions producing maleic anhydride.

43. The process defined in claim 42 including contacting the hydrocarbon with the catalyst in the presence of a gas containing molecular oxygen.

44. A method as defined in claim 1 wherein said crystalline silica comprises silicalite.

45. A method as defined in claim 5 wherein said crystalline silica comprises silicalite.

46. A process as defined in claim 39 wherein said crystalline silica comprises silicalite.

47. A method as defined in claim 1, 2, 10, 15, 20, 21, 23, 27, 28, 32, 33, 44, or 45 wherein said catalyst is prepared by a method comprising:

(A) forming a catalyst precursor by reacting a vanadium compound and a phosphorus compound in an acidic aqueous solution with a divalent tin compound under reaction conditions which will provide vanadium having an average oxidation state of 3.50 to 4.90;
(B) combining the catalyst precursor with a microporous crystalline silica; and
(C) calcining the resultant material at an elevated temperature.

48. A process as defined in claim 39, 40, 41, 42, 43, or 46 wherein said catalyst is prepared by a method comprising:
   (A) forming a catalyst precursor by reacting a vanadium compound and a phosphorous compound in an acidic aqueous solution with a divalent tin compound under reaction conditions which will provide vanadium having an average oxidation state of 3.50 to 4.90;
   (B) combining the catalyst precursor with a microporous crystalline silica; and
   (C) calcining the resultant material at an elevated temperature.

49. A method as defined in claim 1, 2, 5, 15, 27, 32, 33, 38, 44, or 45 wherein said catalyst contains vanadium in an average valence state in the range of 3.5 to 4.9.

50. A method as defined in claim 49 wherein said catalyst has surface area from 100 to 450 $M^2/gm$, and said vanadium is in an average valence state in the range of 4.1 to 4.7.

51. A process as defined in claim 39, 42, 43, or 46 wherein said catalyst contains vanadium in an average valence state in the range of 3.5 to 4.9.

52. A process as defined in claim 51 wherein said catalyst has surface area from 100 to 450 $M^2/gm$, and said vanadium is in an average valence state in the range of 4.1 to 4.7.

* * * * *